(12) United States Patent
Hu

(10) Patent No.: US 10,842,903 B2
(45) Date of Patent: Nov. 24, 2020

(54) AROMA DIFFUSER AND OIL SUPPLY METHOD

(71) Applicant: SHENZHEN NEARBYEXPRESS TECHNOLOGY DEVELOPMENT COMPANY LIMITED, Guangdong (CN)

(72) Inventor: Shuyun Hu, Shenzhen (CN)

(73) Assignee: SHENZHEN NEARBYEXPRESS TECHNOLOGY DEVELOPMENT COMPANY LIMITED, Shenzhen (CN)

(*) Notice: Subject to any disclaimer, the term of this patent is extended or adjusted under 35 U.S.C. 154(b) by 0 days.

(21) Appl. No.: 16/540,078

(22) Filed: Aug. 14, 2019

(65) Prior Publication Data

US 2019/0365942 A1 Dec. 5, 2019

Related U.S. Application Data

(63) Continuation-in-part of application No. PCT/CN2018/094483, filed on Jul. 4, 2018, and a continuation-in-part of application No. 16/357,414, filed on Mar. 19, 2019, now Pat. No. 10,426,860, which is a continuation of application No. PCT/CN2018/094483, filed on Jul. 4, 2018.

(30) Foreign Application Priority Data

Nov. 17, 2017 (CN) .......................... 2017 1 1148646

(51) Int. Cl.
*A61L 9/12* (2006.01)
*A61L 9/14* (2006.01)
*B01F 3/04* (2006.01)

(52) U.S. Cl.
CPC .................................. *A61L 9/14* (2013.01); *A61L 9/12* (2013.01); *A61L 9/125* (2013.01); *A61L 2209/13* (2013.01); *B01F 3/04* (2013.01)

(58) Field of Classification Search
CPC ................. B01F 3/04; A61L 9/12; A61L 9/16
USPC .......................................................... 96/222
See application file for complete search history.

(56) References Cited

U.S. PATENT DOCUMENTS

2019/0374965 A1* 12/2019 Hu ........................ B05B 7/0012

FOREIGN PATENT DOCUMENTS

| CN | 102017937 A | 4/2011 |
|---|---|---|
| CN | 203029678 U | 7/2013 |
| CN | 204446899 U | 7/2015 |
| CN | 107753993 A | 3/2018 |
| CN | 208591355 U | 3/2019 |

(Continued)

*Primary Examiner* — Robert A Hopkins
(74) *Attorney, Agent, or Firm* — Metis IP LLC

(57) ABSTRACT

Provided are an aroma diffusing apparatus and an oil supply method. The aroma diffusing apparatus includes a main body and an oil storage tube. The main body is provided with a liquid storage chamber which is configured to store a liquid. The oil storage tube is configured to store an essential oil. When the aroma diffusing apparatus works, a bottom portion of the oil storage tube may be in fluidic communication with the liquid storage chamber thus allowing the essential oil in the oil storage tube to flow from the bottom of the oil storage tube into the liquid storage chamber as the liquid in the liquid storage chamber is being consumed.

20 Claims, 10 Drawing Sheets

(56) References Cited

FOREIGN PATENT DOCUMENTS

JP   H04170963 A   6/1992
KR   2080047393 A   5/2018

* cited by examiner

AROMA DIFFUSER AND OIL SUPPLY METHOD

CROSS-REFERENCES TO RELATED APPLICATIONS

This application is a continuation-in-part of International Application No. PCT/CN2018/094483, filed on Jul. 4, 2018, which claims priority to and benefits of Chinese Patent Application No. 201711148646.4, filed on Nov. 17, 2017; this application is also a continuation-in-part of U.S. patent application Ser. No. 16/357,414, filed on Mar. 19, 2019, which is a continuation of International Application No. PCT/CN2018/094483, filed on Jul. 4, 2018. The contents of each of the above applications are hereby incorporated in their entireties by reference.

TECHNICAL FIELD

The present disclosure relates to the technical field of air-conditioning devices and more particularly relates to an aroma diffuser and an oil supply method.

BACKGROUND

An aroma diffuser is an aromatherapy device. It typically atomizes water mixed with an essential oil by using high-frequency oscillation such as ultrasonic vibration and then diffusing it into the air to make the air full of fragrance.

The aroma diffuser typically supplies the essential oil by oil dripping. That is, the essential oil is dripped into the water all at once. Because it has a density lower than that of water, the essential oil would float on the water surface after being dripped into a tank of the aroma diffuser. As such, when the aroma diffuser is operating, the essential oil concentration in the tank would decrease as the time of operation progresses, because the essential oil and water are atomized and diffused simultaneously. Therefore, the fragrance of the atomized vapor would become increasingly light, resulting in unsatisfactory user experience.

SUMMARY

The present application provides an aroma diffuser which can supply the essential oil to the liquid storage chamber of the aroma diffuser in a continuous and steady manner, thereby reducing the fluctuation of the essential oil concentration and improving the user experience.

The present application provides an aroma diffuser that includes: a main body provided with a liquid storage chamber, where the liquid storage chamber may be configured to store liquid; and an oil storage tube, which is configured to store essential oil. When the aroma diffuser works normally, the bottom portion of the oil storage tube may be in fluidic communication with the liquid storage chamber, so that the essential oil in the oil storage tube flows from the bottom of the oil storage tube into the liquid storage chamber with the consumption of the liquid in the liquid storage chamber.

In an embodiment, the bottom of the oil storage tube may be disposed close to a preset lowest liquid level of the liquid storage chamber.

In an embodiment, a top end and a bottom end of the oil storage tube may be open.

In an embodiment, a fixing bracket may be disposed within the main body. The fixing bracket may be configured to fix the oil storage tube.

In an embodiment, the bottom portion of the oil storage tube may be provided with a first sealing member for sealing a cavity of the oil storage tube, and a bottom of the fixing bracket may be provided with a first puncture member. When the oil storage tube is fixed on the fixing bracket, the first sealing member may be punctured by the first puncture member, so that the cavity of the oil storage tube may be in fluidic communication with the liquid storage chamber.

In an embodiment, the first puncture member may include a puncture head and a main part connected to the puncture head. The top of the puncture head may be pointed. The maximum width of a cross section of the puncture head may be greater than that of a cross section of the main part. The cavity may be in fluidic communication with the liquid storage chamber via a periphery of the first puncture member after the first sealing member is punctured by the first puncture member.

In an embodiment, the top portion of the oil storage tube may be provided with a second sealing member for sealing the cavity. The aroma diffuser further includes a top cover. The top cover may be disposed on the main body and located above the fixing bracket. The bottom of the top cover may be provided with a second puncture member. The second puncture member may be configured to puncture the second sealing member.

In an embodiment, the top cover may be a press-type top cover. The second puncture member may move downward and puncture the second sealing member when the top cover is pressed, and the top cover may move upward and away from the second sealing member when the top cover is not pressed.

In an embodiment, the bottom of the top cover may be further provided with an abutment portion. When the top cover is pressed downward, the abutment portion may abut the top portion of the oil storage tube and the oil storage tube may be pushed downward so that the first sealing member is punctured by the first puncture member.

In an embodiment, the bottom of the top cover may be further provided with a rebound device. When the abutment portion abuts the top portion of the oil storage tube, the rebound device may be compressed, and after the abutment portion is separated from the top portion of the oil storage tube, the rebound device may drive the oil storage tube to move upward and away from the first puncture member.

In an embodiment, a side wall of the oil storage tube may be fixedly connected to a side wall of the main body, or the top portion of the oil storage tube may be fixedly connected to an inner side of a top wall of the main body.

In an embodiment, the structure of the oil storage tube may be cylinder-shaped or funnel-shaped.

The present application further provides an oil supply method which continuously and stably supplies essential oil to the water, thereby reducing the fluctuation of the essential oil concentration and improving the user experience.

The present application provides an oil supply method which is applied to the aroma diffuser. The method includes: adding water into the liquid storage chamber, where the water level of the water in the liquid storage chamber may be between the bottom of the oil storage tube and a preset highest oil level of the oil storage tube; and adding essential oil into the oil storage tube, where the oil level of the essential oil in the oil storage tube may be higher than the water level of the water in the liquid storage chamber.

The present application further provides an oil supply method which continuously and stably supplies essential oil to the water, thereby reducing the fluctuation of the essential oil concentration and improving the user experience.

The present application provides an oil supply method which is applied to the aroma diffuser. The method includes: adding water into the liquid storage chamber, and fixing the oil storage tube containing the essential oil on the fixing bracket, and letting the first puncture member puncture the first sealing member. The water level of the water in the liquid storage chamber may be between the bottom of the oil storage tube and a preset highest oil level of the oil storage tube.

The present application further provides an oil supply method which continuously and stably supplies essential oil to the water, thereby reducing the fluctuation of the essential oil concentration and improving the user experience.

The present application provides an oil supply method which is applied to the aroma diffuser. The method includes: adding water into the liquid storage chamber; and fixing the oil storage tube containing the essential oil on the fixing bracket, disposing the top cover on the main body, letting the first puncture member puncture the first sealing member, and letting the second puncture member puncture the second sealing member.

The water level of the water in the liquid storage chamber may be between the bottom of the oil storage tube and a preset highest oil level of the oil storage tube.

The present application provides an aroma diffuser and an oil supply method. When liquid such as water is stored in the liquid storage chamber and the essential oil is stored in the oil storage tube, since the bottom of the oil storage tube may be in fluidic communication with the liquid storage chamber, the essential oil at the bottom of the oil storage tube flows into the water for atomization. Since the compatibility of the essential oil and water is poor and the density of the essential oil is lower than that of water, most of the essential oil may be still supported by the water and stored in the oil storage tube. During the use of the aroma diffuser, since the water level continues to descend, the essential oil will descend under the action of gravity, flowing from the bottom of the oil storage tube into the water. Compared with the way of oil dripping in the related art, the essential oil in the oil storage tube may be continuously supplied to the water as the water level descends, reducing the fluctuation of the essential oil concentration in the water, so that fragrance of the atomized vapor is kept stable and the user experience is improved.

Figure 1:
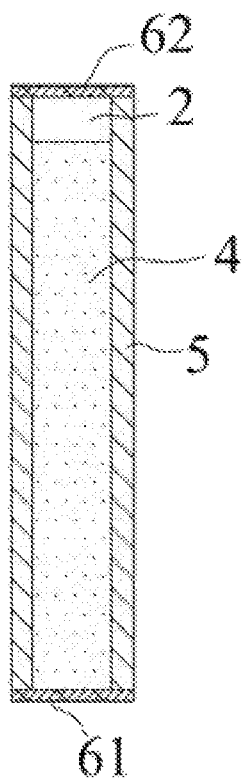
FIG. 1 is a structure diagram of an oil storage tube according to an embodiment of the present application.

In drawings: 1—main body, 11—liquid storage chamber, 2—cavity, 3—liquid, 4—essential oil, 5—oil storage tube, 61—first sealing member, 62—second sealing member, 7—fixing bracket, 71—first puncture member, 8—top cover, 81—second puncture member, and 82—abutment portion.

DETAILED DESCRIPTION

The solutions of the present application are described hereinafter through specific embodiments in conjunction with the drawings.

In the description of the present application, it is to be understood that the orientation or position relationships indicated by terms "above", "below", "front", "back", "left", "right", "vertical", "horizontal", "top", "bottom", "inside", "outside" and the like are based on the orientation or position relationships shown in the drawings, merely for facilitating description of the present application and simplifying description, and these relationships do not indicate or imply that the referred apparatus or element has a specific orientation and is constructed and operated in a specific orientation, and thus it is not to be construed as limiting the present application.

Embodiment 1

Figure 2:
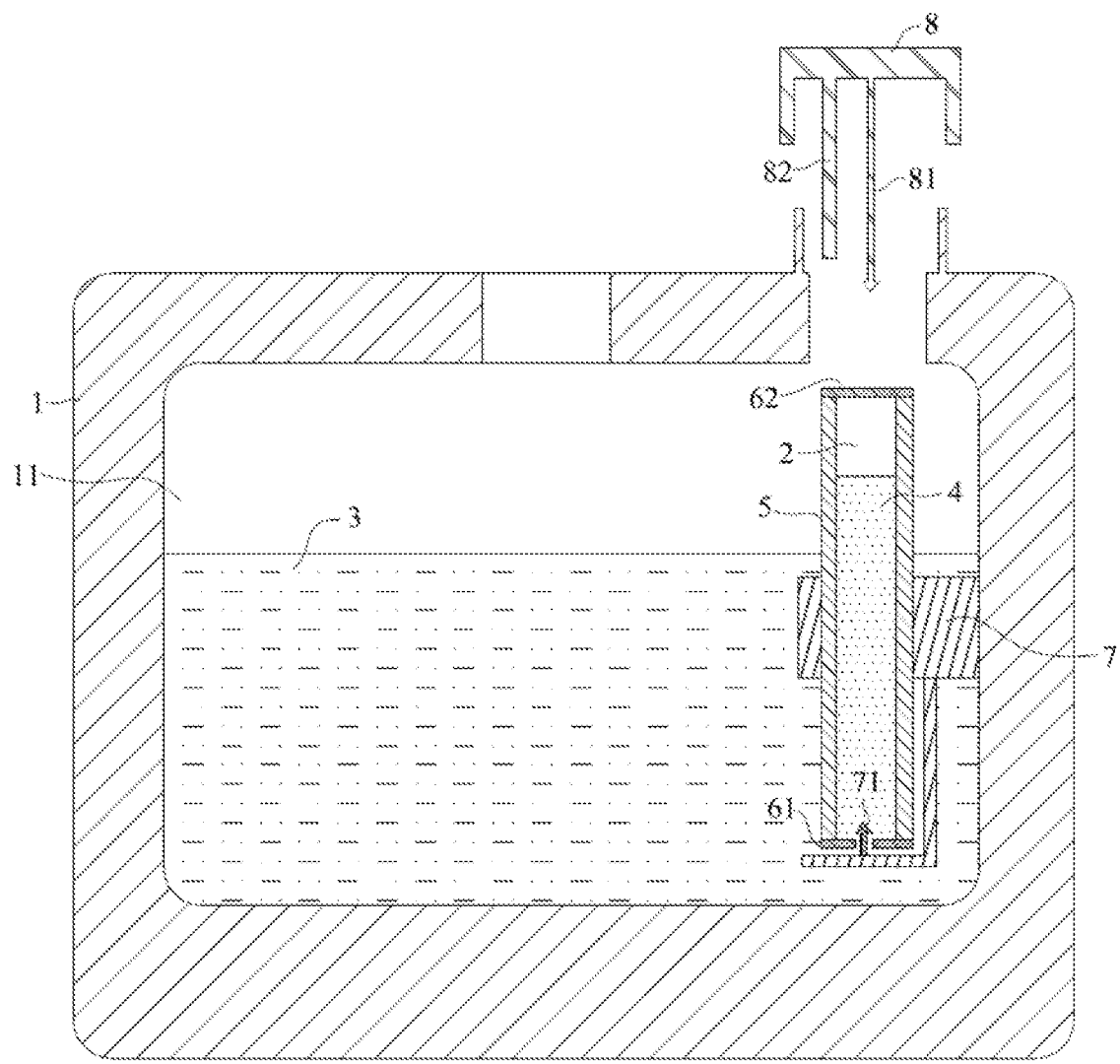
FIG. 2 is a schematic diagram of an aroma diffuser assembled with the oil storage tube according to an embodiment of the present application.
Figure 3:
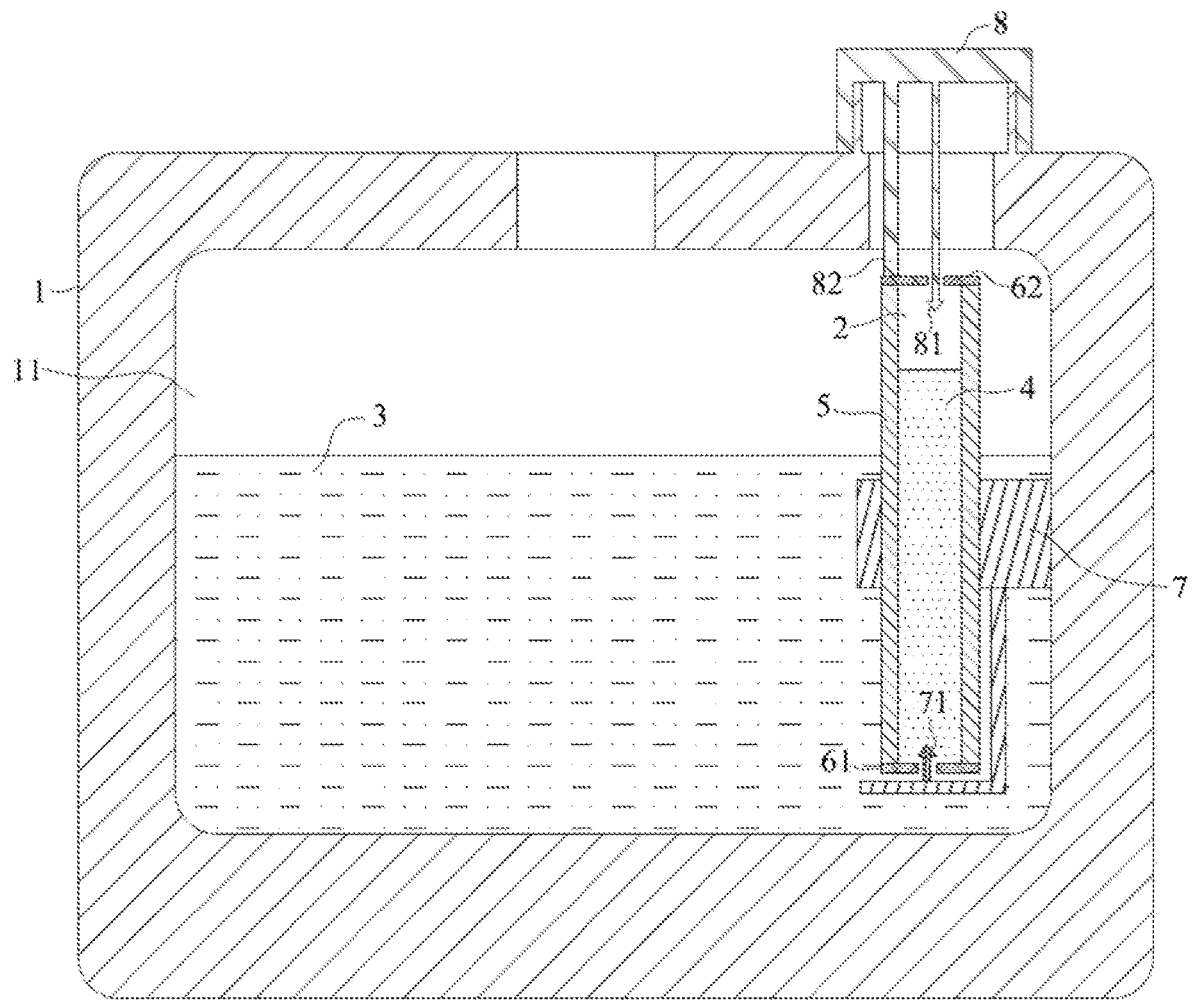
FIG. 3 is a structure diagram illustrating the situation when the aroma diffuser is working according to an embodiment of the present application.

As shown in FIGS. 1 to 5, the present application provides an aroma diffuser which is configured to release an atomized liquid such as water mixed with the essential oil into the air. The aroma diffuser may include a main body 1 and an oil storage tube 5 which is configured to store an essential oil 4. For example, as shown in FIGS. 2 and 3, a liquid storage chamber 11 may be disposed within the main body 1, and the liquid storage chamber 11 may be configured to store a liquid 3. The liquid 3 may be a liquid such as pure water or water mixed with the essential oil or may be other liquids, which is not limited herein. In general, when the aroma diffuser is assembled and capable of working, the oil storage tube 5 may be disposed within the liquid storage chamber 11 to enable the entire aroma diffuser to be compact. However, the oil storage tube 5 may be separated from the main body 1 or may be integrally disposed in the main body 1. In this embodiment, the oil storage tube 5 may be independent of the main body 1 and have a tubular structure as shown in FIG. 1. During the assembly, the oil storage tube 5 may be fixed within the main body. The oil storage tube 5 may store the essential oil 4 via a cavity 2, and the bottom portion of the oil storage tube 5 may be in fluidic communication with the liquid storage chamber 11, ensuring that the essential oil 4 flows from the oil storage tube 5 into the liquid storage chamber 11.

The main body 1 may be further provided with an atomization apparatus (not shown) such as an ultrasonic atomizing sheet or the like. The liquid 3 in the liquid storage chamber 11 or the liquid 3 in a water tank in fluidic communication with the liquid storage chamber 11 may be atomized by the atomization apparatus, and the mist produced may be then discharged outward through an air outlet pipe (not shown).

During the use of the aroma diffuser, it is necessary to add the liquid 3 such as water into the liquid storage chamber 11 and the essential oil 4 into the oil storage tube 5 in advance.

The liquid level of the essential oil 4 in the oil storage tube 5 may need to be higher than the liquid level of the liquid 3 in the liquid storage chamber 11, so that the essential oil in the oil storage tube 5 may flow from the bottom of the oil storage tube 5 into the liquid storage chamber 11 as the liquid 3 in the liquid storage chamber 11 is consumed.

Figure 4:
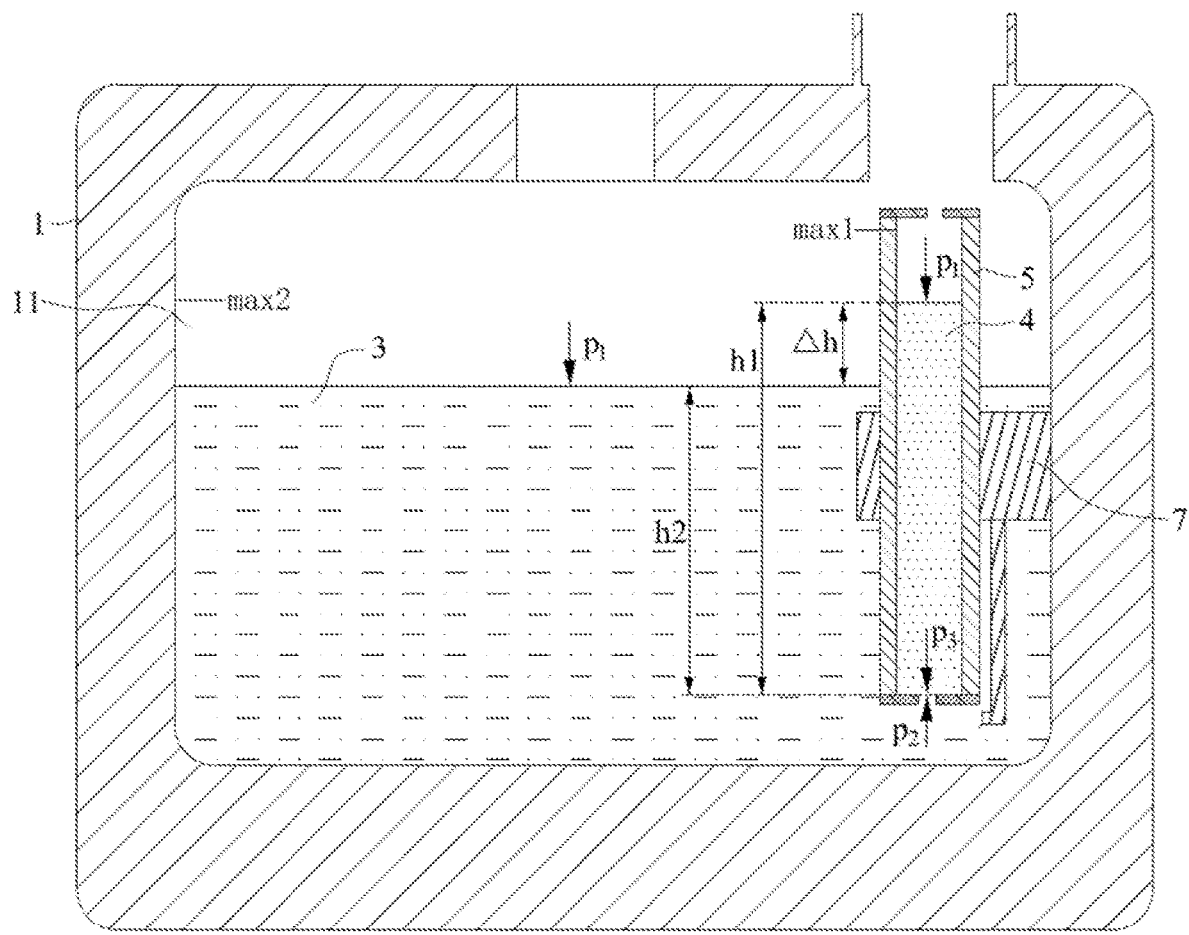
FIG. 4 is a schematic diagram of a force analysis of the essential oil and the liquid in the aroma diffuser according to an embodiment of the present application.

Referring to FIG. 4, since the liquid level of the essential oil 4 in the oil storage tube 5 is higher than the liquid level of the liquid 3 in the liquid storage chamber 11 after the liquid 3 is added into the liquid storage chamber 11 and the essential oil 4 is added into the oil storage tube 5, and due to the poor compatibility between the essential oil 4 and the liquid 3 (in this embodiment, the liquid 3 is mainly water), the essential oil 4 does not rapidly dissolve into the liquid 3 but is still stored in the oil storage tube 5. A used herein, the poor compatibility between the essential oil 4 and the liquid 3 may refer that a solubility of the essential oil 4 in the liquid 3 is smaller than a threshold, such as smaller than 0 g/100 g, or smaller than 0.01 g/100 g, or smaller than 1 g/100 g, etc.

The bottom portion of the oil storage tube 5 may be in fluidic communication with the liquid storage chamber 11, and the area where the essential oil 4 and the liquid 3 contact at the bottom portion of the oil storage tube 5 may be regarded as the bottom surface of the essential oil 4. The distance from the bottom surface of the essential oil 4 to the surface (referring to the top surface where the essential oil 4 contacts with the air) of the essential oil 4 is h1, and the distance from the bottom surface of the essential oil 4 to the surface (referring to the top surface where the liquid 3 contacts with the air) of the liquid 3 is h2. From the analysis based on relevant knowledge in physics, the following conclusions can be obtained.

The air above the liquid 3 is in fluidic communication with the air above the essential oil 4. Since the pressure of the air to the surface of the essential oil 4 is atmospheric pressure p1 and the pressure of the air to the surface of the liquid 3 is also atmospheric pressure p1, which means the air exerts the same pressure to the surface of the liquid 3 as to the surface of the essential oil 4, the pressure of the air to both the essential oil 4 and the liquid 3 is the same and the effect of the pressure of the air is canceled. For the pressure between the liquid 3 and the bottom surface of the essential oil 4, at the bottom surface of the essential oil 4, the pressure of the liquid 3 to the essential oil 4 is $p2=\rho 1gh2$, and the pressure of the essential oil 4 to the liquid 3 is $p3=\rho 2gh1$, where $\rho 1$ is the density of the liquid 3, and $\rho 2$ is the density of the essential oil 4. When $p2=p3$, that is, when $\rho 1gh2=\rho 2gh1$, the height of the essential oil 4 is kept stable. Most of the liquid 3 is water, the density of the essential oil 4 is smaller than that of the liquid 3, that is, $\rho 1>\rho 2$, and correspondingly $h2<h1$. Therefore, the height of the essential oil 4 can be higher than the height of the liquid 3, and the height difference $\Delta h$ between them depends on the density of the liquid 3 and the density of the essential oil 4.

Figure 5:
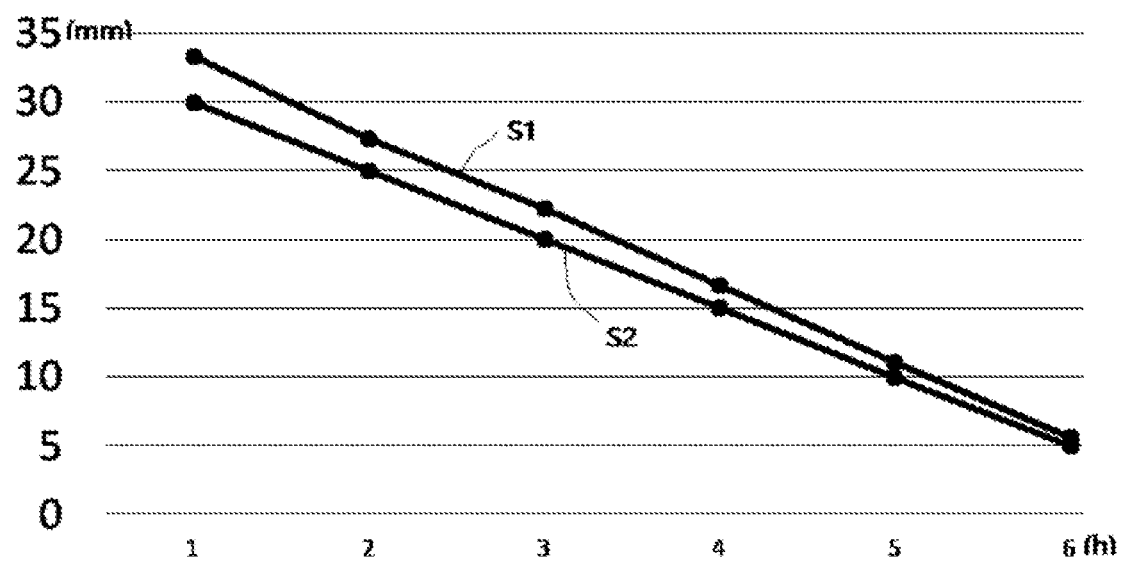
FIG. 5 is a schematic diagram of height changes of the essential oil and the liquid when the aroma diffuser works according to an embodiment of the present application.

From the above analysis, the continuous atomization and consumption of the liquid 3 cause the continuous decrease of h2, and p2 decreases accordingly, resulting in $p2<p3$, which means the pressure exerted to the essential oil 4 by the liquid 3 is lower than the pressure exerted to the liquid 3 by the essential oil 4, or in other words the pressure exerted to the liquid 3 by the essential oil 4 is higher than the pressure exerted to the essential oil 4 by the liquid 3, such that the essential oil 4 will flow into the liquid storage chamber 11 until the balance between the liquid 3 and the essential oil 4 is achieved again. Since $\Delta h=h_1-h_2=(\rho 1/\rho 2-1)h_2$, $\Delta h$ also decreases as h2 decreases, that is, the height difference between the liquid 3 and the essential oil 4 becomes increasingly smaller. In the actual test, the height of the liquid 3 and the height of the essential oil 4 (both with the bottom surface of the liquid storage chamber 11 as the height origin) vary with the atomization time. As shown in FIG. 5. S1 is the curve of the height of the essential oil 4 changing with the atomization time, and S2 is the curve of the height of the liquid 3 changing with the atomization time.

When the aroma diffuser works normally, the bottom portion of the oil storage tube 5 may be in fluidic communication with the liquid storage chamber 11. The liquid 3 such as water may be added into the liquid storage chamber 11 and the essential oil 4 may be added into the oil storage tube 5. The liquid level of the essential oil 4 may need to be higher than the liquid level of the liquid 3. Due to the poor compatibility between the essential oil 4 and the liquid 3 and the higher density of the liquid 3, the essential oil 4 can be kept in the oil storage tube 5. As the aroma diffuser continues to work, the liquid 3 in the liquid storage chamber 11 may be continuously atomized, the liquid level of the liquid 3 continuously may descend, and the liquid level of the essential oil 4 may also continuously descend. The essential oil 4 at the bottom portion may flow into the liquid storage chamber 11 and mixes with the liquid 3, thereby implementing the continuous oil supply to the liquid 3 in the liquid storage chamber 11.

In view of the above, when the aroma diffuser is working normally, the air above the liquid 3 may be in fluidic communication with the air above the essential oil 4, and the pressure of the air to the surface of the liquid 3 is the same as the pressure of the air to the surface of the essential oil 4. As the liquid 3 in the liquid storage chamber 11 is being consumed, at the bottom surface of the essential oil 4, the pressure of the essential oil 4 to the liquid 3 would become stronger than the pressure of the liquid 3 to the essential oil 4, so that the essential oil 4 would flow into the liquid storage chamber 11. Of course, if the essential oil 4 does not yet reach the bottom surface of the oil storage tube 5, the pressure of the essential oil 4 to the liquid 3 would push the bottom surface of the essential oil 4 to move downward to the bottom end of the oil storage tube 5.

Compared with the way that the essential oil is directly dripped into the water in the related art, the aroma diffuser in this embodiment can continuously and stably supply the oil to the liquid 3 in the liquid storage chamber 11. During the use of the aroma diffuser, the concentration of the essential oil 4 may be kept stable, thereby keeping the essential oil concentration in the atomized vapor stable, and avoiding the decrease of the essential oil concentration with the increase of the use time.

In this embodiment, for the convenience of the user, the oil storage tube 5 may be a separate component. The bottom portion of the cavity 2 of the oil storage tube 5 may be provided with a first sealing member 61 for sealing the cavity 2, and the top portion of cavity 2 may be provided with a second sealing member 62 for sealing the cavity 2. The oil storage tube 5 may be made of a plastic, an aluminum, a glass or other materials as long as it is not corroded by the essential oil 4. In addition, the oil storage tube 5 may have better be made of a dark or opaque material to avoid the influence of the light on the essential oil 4 in it. The first sealing member 61 and the second sealing member 62 may be made of aluminum films, plastic films or other materials as long as two ends of the oil storage tube 5 are respectively sealed. Since two ends of the cavity 2 of the oil storage tube 5 need to be sealed, the essential oil 4 may be added into the cavity 2 in advance before two ends of the cavity 2 are sealed. During the use, the user can directly carry or store the oil storage tube 5, and the used oil storage tube 5 in the main body 1 can be replaced with another new oil storage tube 5, thereby greatly improving the portability of the essential oil and offering the convenience to the user.

In order to fix the oil storage tube 5 on the main body 1, a fixing bracket 7 may be disposed within the main body 1, which fixes the oil storage tube 5. The fixing bracket 7 may be a clamping mechanism, such as a clip to clamp the oil storage tube 5. The fixing bracket 7 may also be configured as a structure with a holding hole which can hold the oil storage tube 5, and the holding hole can be tightly joined to the oil storage tube 5. The fixing bracket 7 can be fixed to the main body 1 by means of sticking or fixing via a fastener.

Because both ends of the cavity 2 of the oil storage tube 5 need to be sealed when the oil storage tube 5 is used to store the essential oil, and both ends of the cavity 2 need to be opened when the aroma diffusing apparatus is working thus enabling the upper (or top) end of the cavity 2 to be in fluidic communication with the air inside the liquid storage chamber, so that the essential oil 4 in the cavity 2 may flow into the liquid storage chamber 11. In order to puncture the first sealing member 61 at the bottom portion of the cavity 2, a first puncture member 71 may be disposed on the fixing bracket 7. The first puncture member 71 may be a needle with a sharp end. The first puncture member 71 may be disposed at the bottom portion of the oil storage tube 5. When the oil storage tube 5 is fixed on the fixing bracket 7, the first sealing member 61 can be punctured by the first puncture member 71 to be in fluidic communication with the cavity 2 with the liquid storage chamber 11. In order to puncture the second sealing member 62 at the top portion of the cavity 2, the main body 1 may be provided with a top cover 8 above the fixing bracket 7, and the bottom of the top cover 8 may be provided with a second puncture member 81. When the oil storage tube 5 is installed on the fixing bracket 7 and the top cover 8 is installed on the main body 1, the second sealing member 62 can be punctured by the second puncture member 81 enabling the top of the cavity 2 to be in fluidic communication with the air inside the liquid storage chamber 11. When the apparatus works, both ends of the oil storage tube 5 can be easily punctured through the cooperation of the first puncture member and the second puncture member 72.

In this embodiment, the top cover 8 may be a press-type top cover. The second puncture member 81 may move downward when the top cover 8 is pressed and return upward when the top cover 8 is not pressed. After the top cover 8 is installed on the main body 1, the second puncture member 81 may not contact with the second sealing member 62. When the top cover 8 is pressed downward externally, the second puncture member 81 may move downward to the second sealing member 81 and punctures the second sealing member 62. After that, the second puncture member 81 may move upward and disengage from the oil storage tube 5 to avoid blocking an upper puncture hole formed by the second puncture member 81 puncturing the second sealing member 81.

In order to make the first puncture member 71 easily puncture the first sealing member 61, in this embodiment, an abutment portion 82 may be disposed on the top of the top cover 8. When the top cover 8 is pressed downward, the abutment portion 82 may descend and abut the oil storage tube 5 to drive the oil storage tube 5 to move downward to the first sealing member 61, so that the first sealing member 61 may be punctured by the first puncture member 71.

In order to prevent the first puncture member 71 from blocking the puncture hole to affect the flow of the essential oil after the first sealing member 61 is punctured by the first puncture member 71, the first puncture member 71 may include a puncture head and a main part connected to the puncture head. The top of the puncture head may be pointed. The maximum width of a cross section of the puncture head may be greater than that of a cross section of the main part. When the first puncture member 71 punctures the first sealing member 61 by using its top, a puncture hole having a larger cross section may be formed. Since the bottom of the first puncture member 71 is narrower, a gap may exist between the periphery of the first puncture member 71 and the puncture hole. The cavity 2 may be in fluidic communication with the liquid storage chamber 11 via the periphery of the first puncture member 71. Similarly, the structure of the second puncture member 81 may be similar to that of the first puncture member 71.

Besides the above-mentioned structure configured on the first puncture member 71, a rebound device such as a compression spring may be disposed on the fixing bracket 7 or at the bottom portion of the oil storage tube 5. In an embodiment, the top of the rebound device may carry the oil storage tube 5. When the oil storage tube 5 is pressed downward and the rebound device is compressed, the first sealing member 61 may be punctured by the first puncture member 71. When the pressed oil storage tube 5 is released, the rebound device may drive the oil storage tube 5 to move upward by a certain distance, so that the oil storage tube 5 disengages from the first puncture member 71 to prevent the first puncture member 71 from blocking the puncture hole.

For the aroma diffuser with the oil storage tube 5 of which both ends are sealed, after the essential oil is added in the oil storage tube 5 in advanced and the oil storage tube 5 is sealed, the following steps can be used for supplying the essential oil:

a. adding water into the liquid storage chamber 11;

b. fixing the oil storage tube 5 containing the essential oil 4 on the fixing bracket 7, disposing the top cover 8 on the main body 1, letting the first puncture member 71 puncture the first sealing member 61, and letting the second puncture member 81 puncture the second sealing member 62.

The water level of the water in the liquid storage chamber 11 may be between the bottom of the oil storage tube 5 and a preset highest oil level of the oil storage tube 5.

Through the above-mentioned method, after the first sealing member 61 is punctured by the first puncture member 71 and the second sealing member 62 is punctured by the second puncture member 81, the top portion of the oil storage tube 5 may be in fluidic communication with the liquid storage chamber 11 while the bottom portion of the oil storage tube 5 may be in fluidic communication with the liquid 3 inside the liquid storage chamber 3, so that the oil storage tube 5 can continuously supply oil to the liquid 3 in the liquid storage chamber 11 as the aroma diffuser works.

In this embodiment, the highest water level of the liquid storage chamber 11 refers to the highest area of the water in the liquid storage chamber 11. The highest water level may be preset in a certain position of the liquid storage chamber 11 and the position may be marked to prompt the user (for example, mark the position of max2 in FIG. 4). The highest water level may be a default value, for example, the highest water level may be located at a water inlet on the top of the liquid storage chamber 11. The lowest water level of the liquid storage chamber 11 may be generally at the bottom of the liquid storage chamber 11. The highest oil level refers to the highest area of the essential oil 4 in the oil storage tube 5. The highest oil level may be preset in a certain position of the oil storage tube 5 and the position may be marked to prompt the user (for example, mark the position of max1 in FIG. 4). The highest oil level may be a default position, for example, the highest oil level may be located at the top end of the oil storage tube 5. The lowest oil level may be generally at the bottom of the oil storage tube 5. If the highest water level of the liquid storage chamber 11 is lower than the bottom of the oil storage tube 5, the essential oil 4 in the oil storage tube 5 will completely flow into the water surface of the liquid 3 in the liquid storage chamber 11, and the essential oil 4 cannot be stored, so that the continuous oil supply cannot be implemented. Therefore, the highest water level of the liquid storage chamber 11 may need to be higher than the bottom of the oil storage tube 5. The highest water level of the liquid storage chamber 11 may also need to be lower than the highest oil level of the oil storage tube 5, thereby ensuring that the oil storage tube 5 has oil storage space for storing the essential oil 4 and that the essential oil 4 does not overflow from the top portion of the oil storage tube 5. Therefore, in the actual use, the water level of the water added in the liquid storage chamber 11 needs to be between the bottom of the oil storage tube and the highest oil level.

In this embodiment, the bottom of the oil storage tube 5 may need to be set as close as possible to the lowest liquid level of the liquid storage chamber 11, so that the water in the liquid storage chamber 11 can support the essential oil 4 in the oil storage tube 5 in the process of gradual consumption, thereby obtaining the stable continuous oil supply. If the bottom of the oil storage tube 5 is relatively high, once the water level is lower than the oil storage tube 5, the essential oil 4 will all flow into the liquid 3, which causes a sudden increase of the essential oil concentration, and the gradual decrease of the essential oil concentration subsequently, so that the stable concentration is not maintained.

In some embodiments, an aroma diffuser may include a main body (e.g., the main body 1 as shown in FIGS. 2-4 and 7-10) provided therein with a liquid storage chamber. The liquid storage chamber may be configured to store a liquid. The aroma diffuser may also include an oil storage tube configured to store an essential oil. When the aroma diffuser works, the oil storage tube may be in fluidic communication with the oil storage tube into the liquid storage chamber allowing the essential oil in the oil storage tube to flow or drop from the oil storage tube into the liquid storage chamber along with the consuming of the liquid in the liquid storage chamber. When the aroma diffuser works, the ratio of the volume of the liquid and the volume of the essential oil in the liquid storage chamber may be controlled and/or adjusted in a range along with the consuming of the liquid in the liquid storage chamber. For example, the ratio of the volume of the liquid and the volume of the essential oil in the liquid storage chamber may be kept stable or unchanged along with the consuming of the liquid in the liquid storage chamber. In some embodiments, a bottom portion of the oil storage tube may be in fluidic communication with the liquid storage chamber, allowing the essential oil in the oil storage tube to flow and/or drop from the bottom portion of the oil storage tube into the liquid storage chamber along with the consuming of the liquid in the liquid storage chamber. For example, the bottom portion of the oil storage tube may be installed with an opening. The opening may allow the essential oil in the oil storage tube to flow or drop from the opening of the oil storage tube into the liquid storage chamber along with the consuming of the liquid in the liquid storage chamber. In some embodiments, the bottom portion of the oil storage tube may be installed with a valve configured to control and/or adjust a flow velocity of the essential oil in the oil storage tube when the essential oil in the oil storage tube flows or drops from the opening of the oil storage tube into the liquid storage chamber, which may control and/or adjust the ratio of the volume of the liquid and the volume of the essential oil in the liquid storage chamber. In some embodiments, the aroma diffuser may include a flow velocity measurement sensor configured to detect the flow velocity of the essential oil and/or a controller (e.g., a processor) configured to control and/or adjust the value based on the detected flow velocity. In some embodiments, the controller may be configured to perform speech recognition, facial recognition, etc. A user may control the aroma diffuser via voice. For example, the user may open or close the aroma diffuser via voice. As another example, the user may control the flow velocity of the essential oil, the atomization time of the essential oil, the atomization velocity of the essential oil, etc., via voice. In some embodiments, when the aroma diffuser works, along with the consuming of the liquid in the liquid storage chamber, the ratio of the volume of the liquid and the volume of the essential oil in the liquid storage chamber may be kept stable or unchanged by adjusting the value based on the detected flow velocity. In some embodiments, the ratio of the volume of the liquid and the volume of the essential oil in the liquid storage chamber may be adjusted according to user preference by adjusting the value based on the detected flow velocity. In some embodiments, the aroma diffuser may include multiple oil storage tubes configured to store different essential oils. The aroma diffuser may be connected with a mobile terminal of a user via a wireless connection (e.g., Bluetooth, WiFi) or a wired connection. A user may control the aroma diffuser via the mobile terminal. For example, the user may open or close the aroma diffuser via voice via the mobile terminal. As another example, the user may control the flow velocity of the essential oil, the atomization time of the essential oil, the atomization velocity of the essential oil, etc., via the mobile terminal. As still another example, the user may choose an essential oil stored in which one of the multiple oil storage tubes to flow from the one of the multiple oil storage tubes via the mobile terminal.

In some embodiments, the essential oil in the oil storage tube flows from the oil storage tube into the liquid storage chamber caused by the consuming of the liquid in the liquid storage chamber, a pressure of the essential oil in the oil storage tube to the liquid in the liquid storage chamber is greater than a pressure of the liquid in the liquid storage chamber to the essential oil in the oil storage tube, the essential oil in the oil storage tube has a higher surface than the liquid contained in the liquid storage chamber, air above the liquid is in fluidic communication with air above the essential oil, poor compatibility between the essential oil and the liquid, or the like, or a combination thereof as described elsewhere in the present disclosure. In some embodiments, the essential oil in the oil storage tube may flow from the oil storage tube into the liquid storage chamber caused by an additional pressure supplied to a surface of the essential oil in the oil storage tube by a pressure device. In some embodiments, the aroma diffuser may be provided with the pressure device (not shown) connected with the oil storage tube. The pressure device may be configured to provide the additional pressure to the surface of the essential oil in the oil storage tube when the aroma diffuser works. The pressure device may provide power for the flow of the essential oil to the liquid storage chamber even though the height of the essential oil may be lower than the height of the liquid and/or the air above the liquid is not in fluidic communication with air above the essential oil. In some embodiments, the pressure device may include a gas supplying device that may be configured to supply gas into the oil storage tube when the aroma diffuser works to increase the pressure in the oil storage tube or maintain the pressure in the oil storage tube stable or unchanged as consuming of the essential oil. In some embodiments, the pressure device may include a supercharger. When the aroma diffuser works, the supercharger may increase pressure in the oil storage tube to provide a power for the flow of the essential oil to the liquid storage chamber even though the height of the essential oil may be lower than the height of the liquid and/or the air above the liquid is not in fluidic communication with air above the essential oil. In some embodiments, the supercharger may include a motor and a piston. The motor may be connected with the piston provided in the oil storage tube. The motor may be configured to move the piston in the oil storage tube. In some embodiments, the piston may increase pressure in the oil storage tube by compressing the gas in the oil storage tube. In some embodiments, the piston may contact with the surface of the essential oil in the oil storage tube and push the essential oil to flow into the liquid storage chamber.

Embodiment 2

Figure 6:
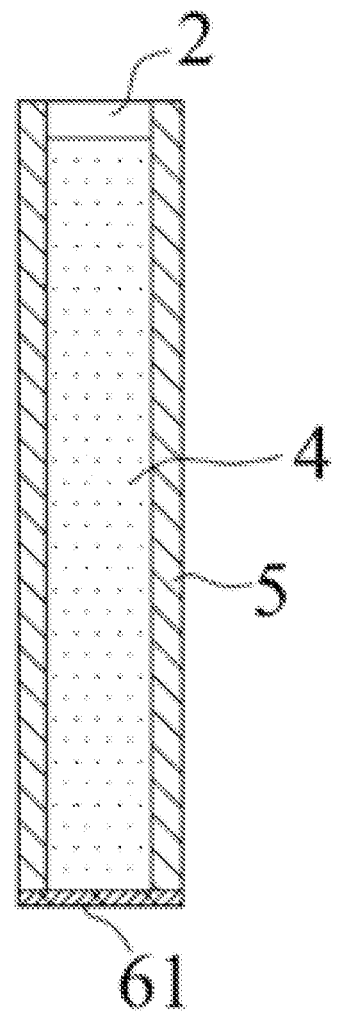
FIG. 6 is a structure diagram of an oil storage tube according to an embodiment of the present application.
Figure 7:
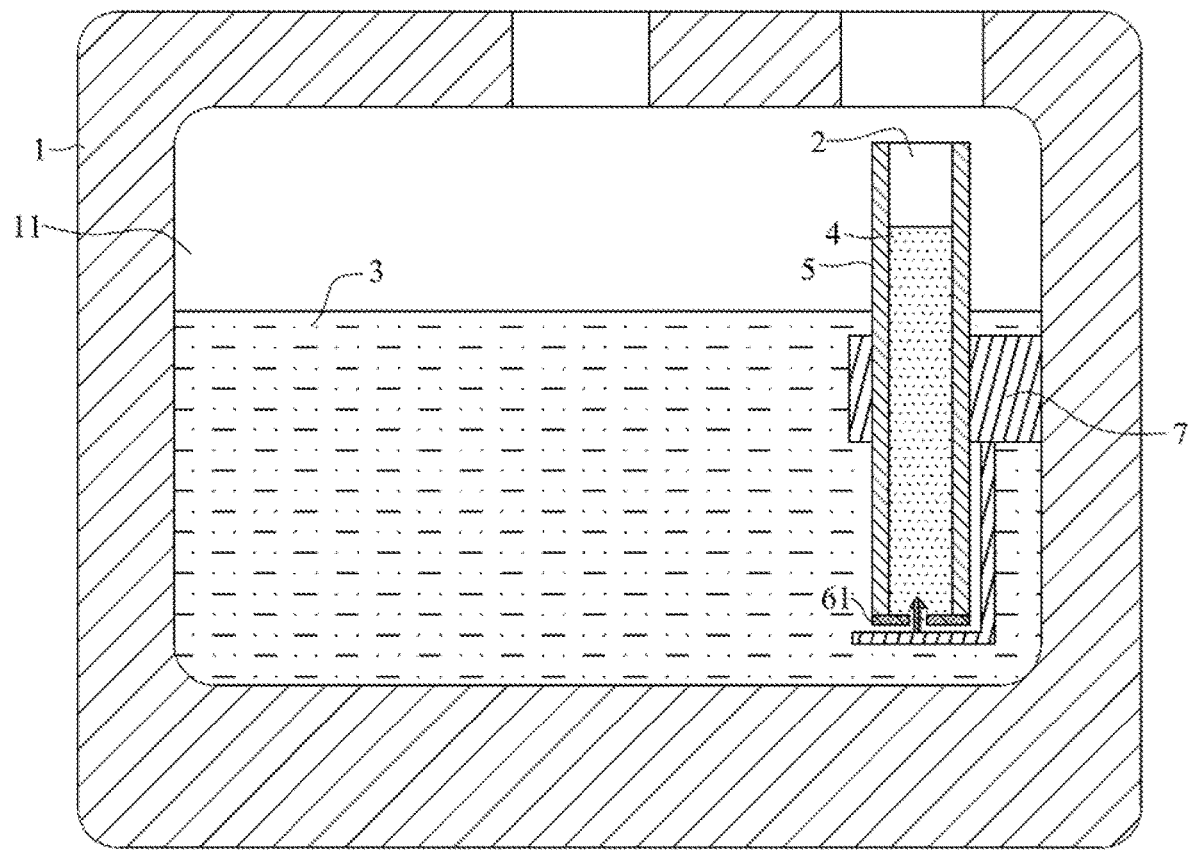
FIG. 7 is a structure diagram of an aroma diffuser according to an embodiment of the present application.

As shown in FIGS. 6 and 7, on the basis of the embodiment 1, the present disclosure provides an aroma diffuser. Different for the embodiment 1, in this embodiment, only one end of the oil storage tube 5 is sealed via the first sealing member 61, and the other end is not sealed.

Correspondingly, since only the bottom end of the oil storage tube 5 is sealed so that the air above the oil storage tube 5 may be in flow fluidic communication with the liquid storage chamber 11. Only the first puncture member 71 may need to be disposed on the fixing bracket 7, and the second puncture member 81 may no longer need to be disposed.

For the bottom-sealed oil storage tube 5, since the bottom of the oil storage tube 5 is sealed, the essential oil 4 may be added in the oil storage tube 5 in advanced. The essential oil is supplied via the following steps below:
  a. adding the liquid 3 into the liquid storage chamber 11;
  b. fixing the oil storage tube 5 containing the essential oil 4 on the fixing bracket 7, and letting the first puncture member 71 puncture the first sealing member 61.

The liquid level of the liquid in the liquid storage chamber 11 may be between the bottom of the oil storage tube 5 and a preset highest oil level of the oil storage tube 5.

Compared with the way that the essential oil is directly dripped into the water in the related art, the aroma diffuser provided in this embodiment can continuously supply the oil to the liquid 3 in the liquid storage chamber 11 in the above-mentioned method after the first sealing member 61 is punctured by the first puncture member 71. As the aroma diffuser continues to work, the liquid 3 in the liquid storage chamber 11 may be continuously atomized, the liquid level of the liquid 3 may continuously descend, so that at the bottom of the essential oil 4, the pressure exerted to the liquid 3 by the essential oil 4 may exceed the pressure exerted to the essential oil 4 by the liquid 3, and the liquid level of the essential oil 4 may also continuously descend. The essential oil 4 at the bottom of the oil storage tube 5 may flow into the liquid storage chamber 11 and mix with the liquid 3, thereby implementing the continuous oil supply to the liquid 3 in the liquid storage chamber 11 and the stable concentration of the essential oil 4 in the liquid 3. Therefore, the essential oil concentration in the atomized vapor may be stable, which avoids the decrease of the essential oil concentration with the increase of the use time. Since the oil storage tube, 5 with the sealed bottom is used, the essential oil 4 can be stored in the oil storage tube 5 in advance. The oil storage tube 5 may be directly fixed on the fixing bracket 7. The first sealing member 61 may be punctured by the first puncture member so that it is not necessary to gradually add the essential oil into the oil storage tube 5, which is very convenient to use.

Except that the second sealing member 62 and the second puncture member 81 are not provided, and that the corresponding use method may be different from that in the embodiment 1, the structure of the aroma diffusing apparatus in this embodiment may be basically the same as that of the embodiment 1, and details are not described herein again.

Embodiment 3

Figure 8:
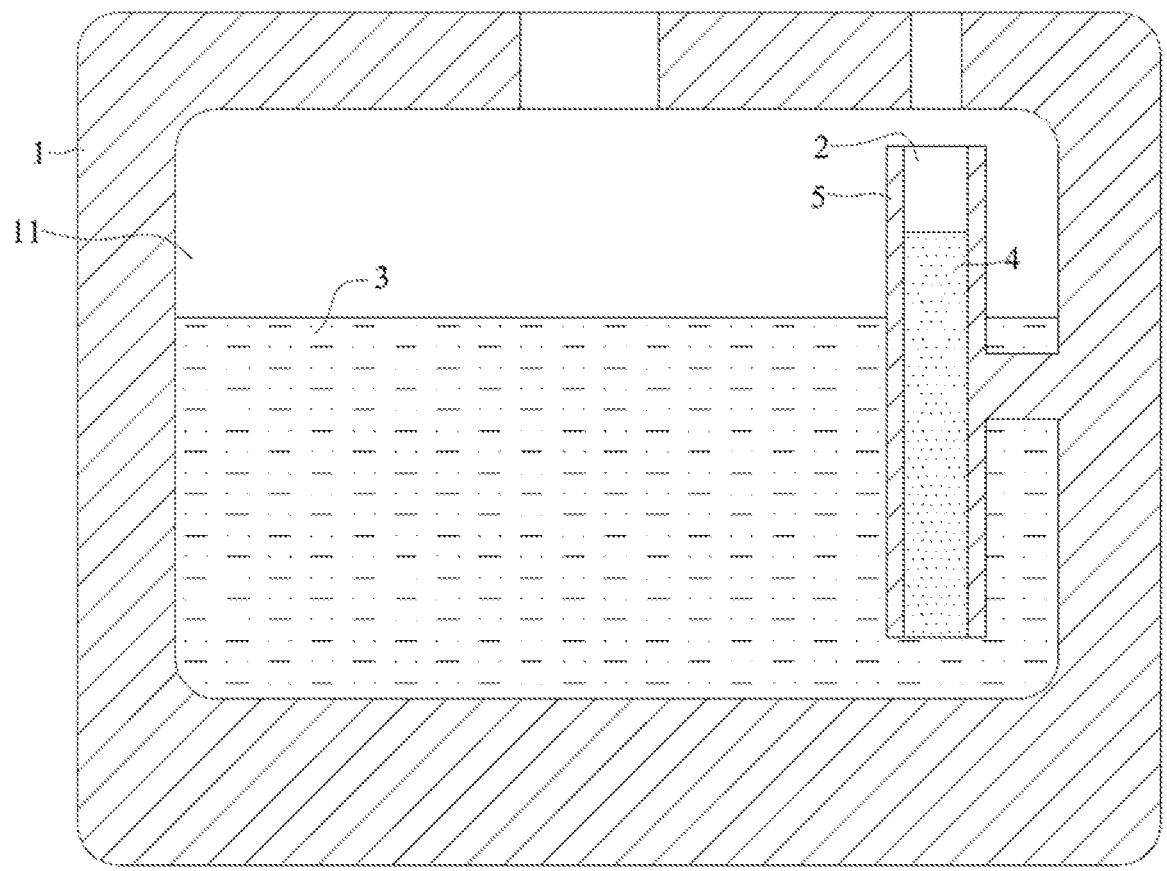
FIG. 8 is a structure diagram of an aroma diffuser according to an embodiment of the present application.
Figure 9:
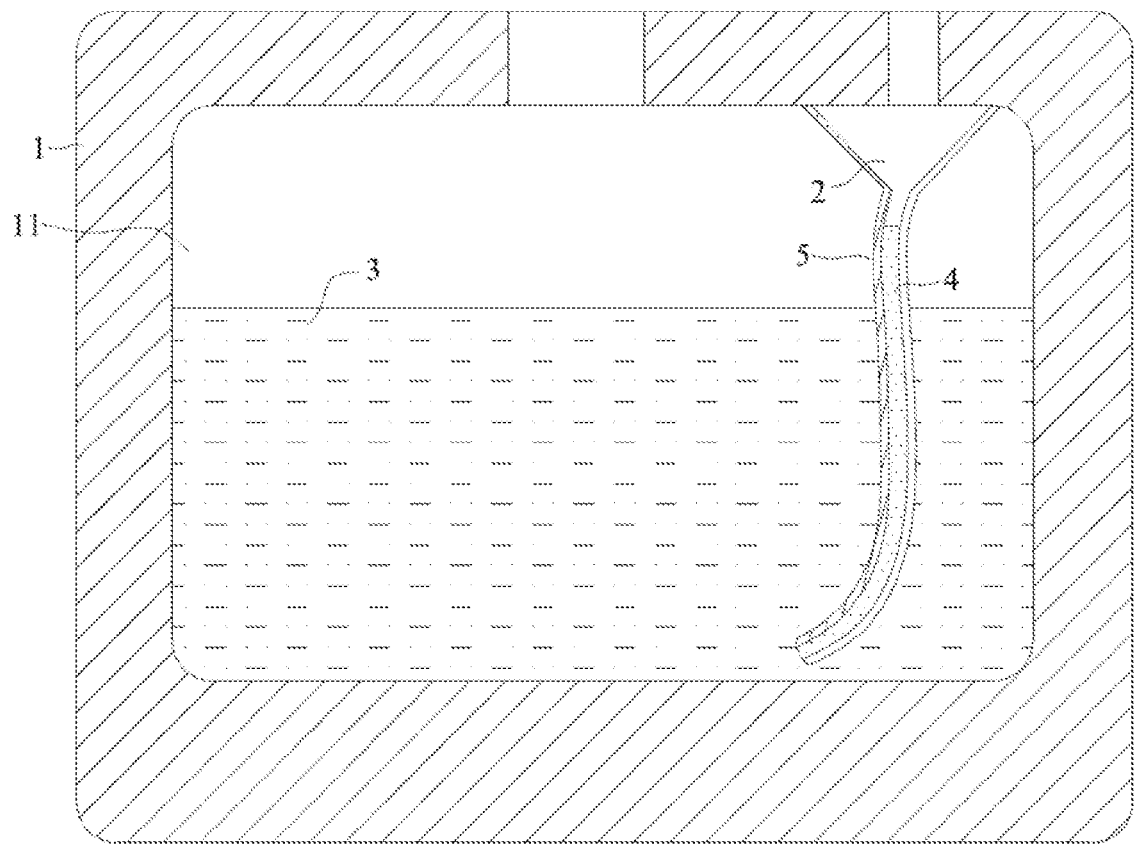
FIG. 9 is a structure diagram of an aroma diffuser according to an embodiment of the present application.

As shown in FIG. 8, on the basis of the embodiment 1, the present disclosure provides an aroma diffuser. Different for the embodiment 1, in the aroma diffuser provided in this embodiment, the oil storage tube 5 may be not a separately configured component, but is directly connected to the main body 1. In general, the top end and the bottom end of the oil storage tube 5 may be open and the top end of the oil storage tube 5 may be in fluidic communication with the liquid storage chamber 11 while the bottom thereof may be in fluidic communication with the liquid 3, so before the aroma diffuser in this embodiment is used, the essential oil 4 can be added via the following steps:
  a. adding water into the liquid storage chamber 11, where the water level of the water in the liquid storage chamber 11 may be between the bottom of the oil storage tube 5 and a preset highest oil level of the oil storage tube 5;
  b. adding the essential oil 4 into the oil storage tube 5.

Compared with the way that the essential oil is directly dripped into the water in the related art, the aroma diffuser provided in this embodiment may store a certain amount of essential oil in the oil storage tube 5 in the above-mentioned method. As the aroma diffuser continues to work, the liquid 3 such as water in the liquid storage chamber 11 may be continuously atomized, the liquid level of the liquid 3 may continuously descend, so that at the bottom of the essential oil 4, the pressure exerted to the liquid 3 by the essential oil 4 may exceed the pressure exerted to the essential oil 4 by the liquid 3, and the liquid level of the essential oil 4 may also continuously descend. The essential oil 4 at the bottom of the oil storage tube 5 may flow into the liquid storage chamber 11 and mix with the liquid 3, thereby implementing the continuous oil supply to the liquid 3 in the liquid storage chamber 11 and the stable concentration of the essential oil 4 in the liquid 3. Therefore, the essential oil concentration in the atomized vapor may be stable, which avoids the decrease of the essential oil concentration with the increase of the use time.

In this embodiment, the oil storage tube 5 may be integrally formed in the main body 1 or may be separately formed and fixed detachably to the main body 1 by means of sticking, clamping, or fixing via a fastener.

The structure of oil storage tube 5 may be various. Besides the design of the hollow cylinder shown in FIG. 1, the oil storage tube 5 may further be designed as a funnel shown in FIG. 5. The top portion of the oil storage tube 5 may be connected to the top wall of the main body 1, and the bottom portion of the funnel-shaped oil storage tube 5 may be inserted into the bottom of the liquid storage chamber 11 via a pipe or the like. All in all, the oil storage tube 5 may be designed as any shape as long as the bottom of the oil storage tube 5 may be in fluidic communication with the liquid storage chamber 11. In this embodiment, the oil storage tube 5 may be disposed within the liquid storage chamber 11 to make the aroma diffuser as a whole. In an embodiment, the oil storage tube 5 may be disposed outside the liquid storage chamber 11. For example, the funnel-shaped oil storage tube 5 shown in FIG. 9 may be disposed outside the liquid storage chamber 11. The bottom portion of the oil storage tube 5 may be inserted into the liquid storage chamber 11, or the bottom of the oil storage tube 5 may be in fluidic communication with the liquid storage chamber 11 via a hole which is opened on the side of the main body 1.

In this embodiment, the main body 1 may be provided with a water inlet and an essential oil inlet on the top portion of the liquid storage chamber 11, and the essential oil inlet may correspond to the oil storage tube 5. The presence of the water inlet and the essential oil inlet enables the air above the liquid inside the liquid storage chamber to be in fluidic communication with the air above the essential oil inside the oil storage tube leading to the same air pressure at the surface of the liquid as that at the surface of the essential oil. The essential oil may be added into the oil storage tube 5 via the essential oil inlet when the essential oil needs to be added. In addition, an essential oil storage tank may be preset on the main body 1 correspondingly. The bottom portion of the essential oil storage tank may be connected to the top portion of the oil storage tube 5 via a passage and a corresponding switch may be provided on the passage. After a certain amount of essential oil is pre-added into the essential oil storage tank, the switch may be turned on, and the essential oil 4 may be gradually added by controlling the degree of open of the switch, so that the user does not need to continuously add the essential oil 4 into the oil storage tube 5.

All in all, the aroma diffuser provided in the present application may store a certain amount of essential oil in the oil storage tube 5. When the aroma diffuser works normally, the bottom portion of the oil storage tube 5 may be in fluidic communication with the liquid storage chamber 11, and the essential oil 4 can be kept in the oil storage tube 5 due to the poor compatibility between the essential oil 4 and the liquid 3 and the higher density of the liquid 3. Because the air applies the same pressure to surface of the liquid 3 as to the surface of the essential oil 4, as the aroma diffuser continues to work, the liquid 3 in the liquid storage chamber 11 may be continuously atomized, the liquid level may continuously descend while at the bottom of the essential oil the pressure exerted to the liquid 3 by the essential oil 4 exceeds the pressure exerted to the essential oil 4 by the liquid 3, and the liquid level of the essential oil 4 may also continuously descends. The essential oil 4 at the bottom of the oil storage tube 5 may flow into the liquid storage chamber 11 and mix with the liquid 3, thereby implementing the continuous oil supply to the liquid 3 in the liquid storage chamber 11.

Figure 10:
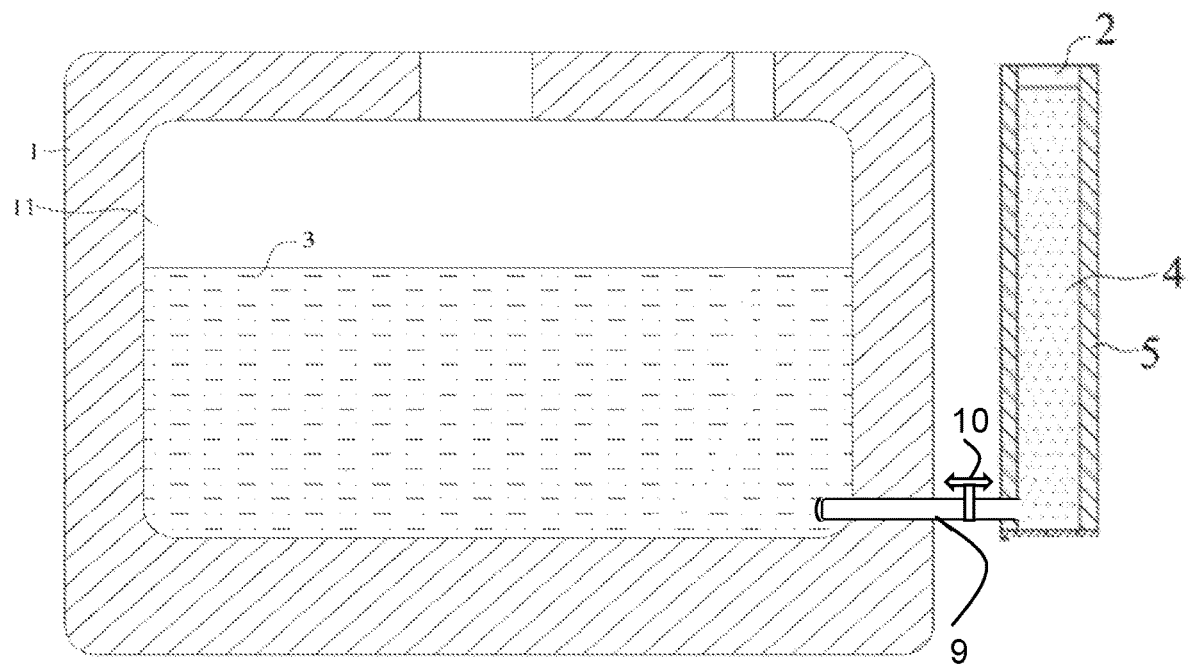
FIG. 10 is a schematic diagram of an aroma diffuser assembled with the oil storage tube according to some embodiments of the present application.

FIG. 10 is a schematic diagram of an aroma diffuser assembled with the oil storage tube according to some embodiment of the present application. As shown in FIG. 10, an aroma diffuser may include a main body 1 and an oil storage tube 5. The main body 1 may be provided therein with a liquid storage chamber 11. The liquid storage chamber 11 may be configured to store a liquid 3, such as water. The oil storage tube 5 may include a cavity 2 configured to store an essential oil 4. The oil storage tube 5 may be located and/or mounted outside of the main body 1. For example, the oil storage tube 5 may be located and/or mounted above the main body 1. In some embodiments, a bottom portion of the oil storage tube 5 may be in fluidic communication with the liquid storage chamber 11, allowing the essential oil 4 in the oil storage tube 5 to flow and/or drop from the bottom portion of the oil storage tube 5 into the liquid storage chamber 11 along with the consuming of the liquid in the liquid 3 storage chamber 11. For example, the bottom portion of the oil storage tube 5 may be installed with an opening. The opening may allow the essential oil 4 in the oil storage tube 5 to flow or drop from the opening of the oil storage tube 5 into the liquid storage chamber 11 along with the consuming of the liquid in the liquid storage chamber 11. In some embodiments, the bottom portion of the oil storage tube 5 may be installed with a valve configured to control and/or adjust a flow velocity of the essential oil 4 in the oil storage tube 5 when the essential oil 4 in the oil storage tube 5 flows or drops from the opening of the oil storage tube 5 into the liquid storage chamber 11 to control and/or adjust the concentration of the liquid 3 and the essential oil in the liquid storage chamber 11. For example, when the aroma diffuser works, along with the consuming of the liquid in the liquid storage chamber 11, the concentration of the liquid 3 and the essential oil in the liquid storage chamber 11 may be kept stable or unchanged. As another example, the concentration of the liquid 3 and the essential oil in the liquid storage chamber 11 may be adjusted according to user preference.

In some embodiments, a bottom portion of the main body 1 may be also installed with an opening. The oil storage tube 5 may be in fluidic communication with the liquid storage chamber 11 via the openings installed on the oil storage tube 5 and the liquid storage chamber 11, respectively. The essential oil 4 may flow from the oil storage tube 5 to the liquid storage chamber 11 via the openings as elsewhere in the present disclosure. In some embodiments, the oil storage tube 5 may be in fluidic communication with the liquid storage chamber 11 via a pipe 9. The pipe 9 may be made of a plastic material, a metal material, a rubber material, etc. Two ends of the pipe 9 may be connected fixedly or detachably with the oil storage tube 5 and the liquid storage chamber 11, respectively. The essential oil 4 may flow from the oil storage tube 5 to the liquid storage chamber 11 via the pipe 9. In some embodiments, the pipe 9 may be installed with a valve 10. In some embodiments, the openings of the oil storage tube 5 and/or the liquid storage chamber 11 may be installed with a valve. The valve 10 installed on the pipe 9 or valves installed on the oil storage tube 5 and/or the main body 1 may be configured to prevent the essential oil 4 to flow from the oil storage tube 5 to the liquid storage chamber 11 when the aroma diffuser does not work. In some embodiments, the oil storage tube 5 may be fixedly connected with the main body 1. For example, the oil storage tube 5, the main body 1, and/or the pipe 9 may be integrally formed. As another example, the oil storage tube 5, the main body 1, and/or the pipe 9 may be connected by a welding technique. In some embodiments, the oil storage tube 5 may be connected with the main body 1 detachably. For example, the oil storage tube 5 may be connected with the main body 1 via a thread connection technique. As another example, the oil storage tube 5 may be connected with the main body 1 via the pipe 9 detachably using the thread connection technique.

In some embodiments, the top of the oil storage tube 2 may include a second sealing member as described elsewhere. The second sealing member may be connected with the oil storage tube 2 detachably or fixedly. For example, a user may add the essential oil 4 into the oil storage tube 5 by removing the second sealing member when the essential oil 4 are few or depleted. As another example, when the aroma diffuser works, a user may remove the second sealing member to make air above the liquid 3 in fluidic communication with air above the essential oil 4. When the aroma diffuser works normally, the bottom portion of the oil storage tube 5 may be in fluidic communication with the liquid storage chamber 11. The liquid 3 such as water may be added into the liquid storage chamber 11 and the essential oil 4 may be added into the oil storage tube 5. The liquid level of the essential oil 4 may need to be higher than the liquid level of the liquid 3. Due to the poor compatibility between the essential oil 4 and the liquid 3 and the higher density of the liquid 3, the essential oil 4 can be kept in the oil storage tube 5. As the aroma diffuser continues to work, the liquid 3 in the liquid storage chamber 11 may be continuously atomized, the liquid level of the liquid 3 continuously may descend, and the liquid level of the essential oil 4 may also continuously descend. The essential oil 4 at the bottom portion may flow into the liquid storage chamber 11 and mixes with the liquid 3, thereby implementing the continuous oil supply to the liquid 3 in the liquid storage chamber 11

In some embodiments, the aroma diffuser may be configured with a pressure device (not shown) connected with the oil storage tube 5. The pressure device may be configured to provide an additional pressure to the surface of the essential oil 4 in the oil storage tube 5 when the aroma diffuser works. The pressure device may provide a power for the flow of the essential oil 4 to the liquid storage chamber 11 even though the height of the essential oil 4 is lower than the height of the liquid 3 and/or the air above the liquid 3 is not in fluidic communication with air above the essential oil 4. In some embodiments, the pressure device may include a gas supplying device that may be configured to supply gas into the oil storage tube 5 when the aroma diffuser works to increase the pressure in the oil storage tube 5 or maintain the pressure in the oil storage tube 5 stable or unchanged as consuming of the essential oil 4. In some embodiments, the pressure device may include a supercharger. When the aroma diffuser works, the supercharger may increase pressure in the oil storage tube 5 to provide a power for the flow of the essential oil 4 to the liquid storage chamber 11 even though the height of the essential oil 4 is lower than the height of the liquid 3 and/or the air above the liquid 3 is not in fluidic communication with air above the essential oil 4. In some embodiments, the supercharger may include a motor and a piston. The motor may be connected with the piston provided in the oil storage tube 5. The motor may be configured to provide power for the movement of the piston in the oil storage tube 5. In some embodiments, the piston may increase the pressure in the oil storage tube 5 by compressing the gas in the oil storage tube 5. In some embodiments, the piston may contact with the surface of the essential oil 4 in the oil storage tube 5 and push the essential oil 4 to flow into the liquid storage chamber 11 by supplying a force on the surface of the essential oil 4.

Compared with the way that the essential oil is directly dripped into the water in the related art, the aroma diffuser in this embodiment can continuously and stably supply the oil to the liquid 3 in the liquid storage chamber 11. During the use of the aroma diffuser, the concentration of the essential oil 4 may be kept stable, thereby keeping the essential oil concentration in the atomized vapor stable, and avoiding the decrease of the essential oil concentration with the increase of the use time. The above-mentioned content is the embodiments of the present application, and the content of this specification is not to be construed as limiting the present disclosure.

What is claimed is:

1. An aroma diffuser, comprising:
    a main body, provided therein with a liquid storage chamber, the liquid storage chamber being configured to store a liquid; and
    an oil storage tube configured to store an essential oil,
    wherein when the aroma diffuser works, the oil storage tube is in fluidic communication with the liquid storage chamber, allowing the essential oil in the oil storage tube to flow from the oil storage tube into the liquid storage chamber along with consuming of the liquid in the liquid storage chamber.

2. The aroma diffuser according to claim 1, wherein when the aroma diffuser works, a ratio of a volume of the liquid and a volume of an essential oil in the liquid storage chamber is within a predetermined range.

3. The aroma diffuser according to claim 1, wherein when the aroma diffuser works, a pressure of the essential oil in the oil storage tube to the liquid in the liquid storage chamber is greater than a pressure of the liquid in the liquid storage chamber to the essential oil in the oil storage tube, allowing the essential oil in the oil storage tube to flow from the oil storage tube into the liquid storage chamber along with consuming of the liquid in the liquid storage chamber.

4. The aroma diffuser according to claim 1, wherein when the aroma diffuser works, a bottom portion of the oil storage tube is in fluidic communication with the liquid storage chamber, allowing the essential oil in the oil storage tube to flow from the bottom portion of the oil storage tube into the liquid storage chamber along with the consuming of the liquid in the liquid storage chamber.

5. The aroma diffuser according to claim 4, wherein the oil storage tube is configured to store the essential oil when the bottom portion of the oil storage tube is in fluidic communication with the liquid storage chamber as a solubility of the essential oil in the liquid is smaller than a threshold.

6. The aroma diffuser according to claim 4, wherein the oil storage tube is configured to store the essential oil when the bottom portion of the oil storage tube is in fluidic communication with the liquid storage chamber as the liquid is water.

7. The aroma diffuser according to claim 4, wherein when the aroma diffuser works, the essential oil in the oil storage tube flows from the bottom portion of the oil storage tube into the liquid storage chamber caused by the consuming of the liquid in the liquid storage chamber.

8. The aroma diffuser according to claim 4, wherein when the aroma diffuser works, the essential oil in the oil storage tube has a higher surface than the liquid contained in the liquid storage chamber, allowing the essential oil in the oil storage tube to flow from the bottom portion of the oil storage tube into the liquid storage chamber along with consuming of the liquid in the liquid storage chamber.

9. The aroma diffuser according to claim 4, wherein when the aroma diffuser works, air above the liquid is in fluidic communication with air above the essential oil allowing the essential oil in the oil storage tube to flow from the bottom portion of the oil storage tube into the liquid storage chamber along with consuming of the liquid in the liquid storage chamber.

10. The aroma diffuser according to claim 1, further comprising:
   a pressure device configured to provide an additional pressure to a surface of the essential oil in the oil storage tube, the additional pressure allowing the essential oil in the oil storage tube to flow from the oil storage tube to the liquid storage chamber along with consuming of the liquid in the liquid storage chamber.

11. The aroma diffuser according to claim 1, wherein the pressure device includes a motor and a piston, and the motor is configured to provide a power to drive moving of the piston, the moving of the piston generating the additional pressure.

12. The aroma diffuser according to claim 1, wherein the oil storage tube is mounted inside of the main body.

13. The aroma diffuser according to claim 12, wherein a bottom of the oil storage tube is disposed in proximity to a preset lowest liquid level of the liquid storage chamber.

14. The aroma diffuser according to claim 12, wherein the main body includes a fixing bracket that is disposed within the main body, and is configured to fix the oil storage tube in the liquid storage chamber.

15. The aroma diffuser according to claim 14, wherein a bottom portion of the oil storage tube is provided with a first sealing member for sealing a cavity of the oil storage tube, and a bottom of the fixing bracket is provided with a first puncture member, wherein the first puncture member is configured to puncture the first sealing member when the oil storage tube is fixed to the fixing bracket, allowing the cavity of the oil storage tube to be in fluidic communication with the liquid storage chamber.

16. The aroma diffuser apparatus according to claim 15, wherein a top portion of the oil storage tube is provided with a second sealing member for sealing the cavity; and
   the aroma diffuser includes a second puncture member configured to puncture the second sealing member, allowing the cavity of the oil storage tube to be in fluidic communication with the liquid storage chamber.

17. The aroma diffuser according to claim 1, wherein a side wall of the oil storage tube is fixedly connected to a side wall of the main body or a top portion of the oil storage tube is fixedly connected to an inner side of a top wall of the main body.

18. The aroma diffuser according to claim 1, wherein the oil storage tube is mounted outside the liquid storage chamber.

19. The aroma diffuser according to claim 18, wherein the oil storage tube is in fluidic communication with the liquid storage chamber via a pipe.

20. An oil supply method, applied to an aroma diffuser including a main body, provided therein with a liquid storage chamber configured to store a liquid and an oil storage tube configured to store an essential oil, the method comprising:
   adding the liquid into the liquid storage chamber; and
   adding the essential oil into the oil storage tube,
   when the aroma diffuser works, the oil storage tube is in fluidic communication with the liquid storage chamber, allowing the essential oil in the oil storage tube to flow from the oil storage tube into the liquid storage chamber along with consuming of the liquid in the liquid storage chamber.

* * * * *